United States Patent [19]

Brown, Jr. et al.

[11] Patent Number: 4,891,317
[45] Date of Patent: Jan. 2, 1990

[54] MAGNETIC ALTERNATION OF CELLULOSE DURING ITS BIOSYNTHESIS

[75] Inventors: R. Malcolm Brown, Jr., Austin, Tex.; Debra S. Brown, Pasadena, Calif.; Michael R. Gretz, Austin, Tex.

[73] Assignee: Board of Regents, The University of Texas System, Austin, Tex.

[21] Appl. No.: 719,505

[22] Filed: Apr. 3, 1985

[51] Int. Cl.$^4$ .................. C12P 19/04; C12N 13/00; C12N 1/20; A01G 7/04

[52] U.S. Cl. ........................ 435/101; 435/173; 435/252.1; 435/822; 47/1.3

[58] Field of Search ............... 435/173, 101, 240.4, 435/253, 822, 823, 829, 875, 878; 47/1.3

[56] References Cited

U.S. PATENT DOCUMENTS

| | | | |
|---|---|---|---|
| 3,910,233 | 10/1975 | Amburn | 119/1 |
| 3,991,714 | 11/1976 | Amburn | 119/1 |
| 4,020,590 | 5/1977 | Davis | 47/1.3 |
| 4,065,386 | 12/1977 | Rigby | 210/60 |
| 4,378,431 | 3/1983 | Brown, Jr. | 435/101 |

FOREIGN PATENT DOCUMENTS

| | | | |
|---|---|---|---|
| 2451707 | 11/1980 | France | 47/1.3 |
| 0663358 | 5/1979 | U.S.S.R. | 47/1.3 |
| 0917783 | 4/1982 | U.S.S.R. | 47/1.3 |
| 0974951 | 11/1982 | U.S.S.R. | 47/1.3 |

OTHER PUBLICATIONS

Moustafa et al, 13th Ann. Meet. Am. Soc. Agr. Eng. (1973) pp. 1–11.
European Search Report, GJB 70/2616/02; Board of Regents The University of Texas System.
T. P. Nevell et al., "Cellulose chemistry and its applications", 1985, pp. 30,31, 67–73,76,79,80,82,83, Ellis Horwood Ltd, Chichester, GB; C. H. Haigler: The functions and biogenesis of native cellulose.
Chemical Abstract, vol. 76, No. 18, 1st May 1972, p. 128, abstract No. 101767e, Columbus, Ohio, U.S.; & CS-A-139 856 (P. Zuffa) 15-01-1971.
Chemical Abstract, vol. 97, No. 13, 27th Sep. 1982, p. 480, abstract No. 108516q, Columbus, Ohio, U.S.; & JP-A-82 79 881 (TDK Electronics Co., Ltd) 19-0-5-1982.
Greenebaum et al (1982) Europ. J. Cell. Biol. V27 pp. 156–160.
Gaffney et al (1974) Chem. Physics Lett. V24 pp. 310–313.
Liboff et al. (1984) Science V223 pp. 818–820.
Cope (1981) Physiol. Chem. & Physics (1981) V13 pp. 567–568.
Adey (1981) Physiol. Revs. V61 pp. 435–514.
Audus (1960) Nature V185 pp. 132–134.
Papp et al (1982) Biophys. J. V39 pp. 1–5.
McKenzie et al (1980) Can. J. Plant Sci. V60 pp. 87–90.
Harmet (1982) Plany Physiol. V69 Suppl. p. 125.
Geacintov et al (1972) Biochem. et Biophys. Acta V267 pp. 65–79.
Brown, Jr. et al (1983) J. Appl Polymer Sci: Appl. Polymer Symp. V37 pp. 33–78.
Brown, Jr. et al (1982) Science V218 pp. 1141–1142.
Brown, Jr. et al (1976) Proc. Natl. Acad. Sci. V73 pp. 4565–4569.
Haigler et al. (1982) Cellulose and Other Natural Polymer Systems, ed. R. M. Brown, Jr. Plenum Press, NY.
Bergey's Manual of Systematic Bacterioloy (1984) V1 pp. 268–274.
Purz et al (1977) Faserforshung und Textiltechnik V28 pp. 155–163.
Schwarz et al (1976) Faserforschung und Testiltechnik V27 pp. 561–570.

*Primary Examiner*—John Edward Tarcza
*Attorney, Agent, or Firm*—Arnold, White & Durkee

[57] ABSTRACT

A method of producing cellulose of amorphous character by subjecting cellulose-producing organisms to a magnetic field substantially greater than 0.5 gauss and preferably at least about 500 gauss. The cellulose produced in the presence of a magnetic field is of an amorphous nature with increased water absorptivity and decreased crystallinity.

13 Claims, No Drawings

MAGNETIC ALTERNATION OF CELLULOSE DURING ITS BIOSYNTHESIS

BACKGROUND OF THE INVENTION

The present invention relates generally to amorphous cellulose and disordered cellulose compositions and to methods of making the same. The invention more particularly concerns a method of making altered cellulose by the action of a magnetic field upon cellulose-producing organisms.

Cellulose, a natural polysaccharide found throughout the plant world, is used for many purposes. Cellulosic products are usually obtained in various forms from plants such as trees, after different types of processing. The specific types of processing depend upon the uses to which the final cellulosic product is to be put.

Cellulose may also be obtained from cellulose-producing microorganisms. Such microbial cellulose, similar to plant derived cellulose in chemical structure, may be utilized for many analogous purposes.

The structure of microbial cellulose membranes has been studied by Purz et al (Faserforshung und Textiltechnik V. 28(4) pp. 155-163, 1977 and V. 27(11) pp. 561-570, 1976) and determined to be an interwoven and disordered mesh of fibrillar strands with diameters of 50 mm to 100 mm.

Microbial cellulose has been produced in altered form by chemical alterations on the addition of fluorescent brightening agents or direct cellulose dyes.

Magnetic fields have been implicated as having effects on many living systems. The growth of winter wheat seeds, for example, has been found to be stimulated in a magnetic field of 100 gauss, this stimulation not being further increased by magnetic fields up to 1500 gauss (Cope, Physiol.: Chem. & Physics (1981) V. 13, pp. 567-568). Geacintov et al (Biochem. et Biophys. Acta (1972) V. 267, pp. 65-79 has shown a magnetic orientation effect on chloroplasts and whole Chlorella cells. McKenzie and Pittman (Can. J. Plant Sci. (1980) V. 60, pp. 87-90) demonstrated that magnetotropic root growth is a plant characteristic inheritable through plant cytoplasm. A growth response of Lepidium seedlings exposed to magnetic field gradient was shown by Audus (*Nature* V. 185: pp. 132-134, 1960) and oriented growth of pollen tubes in a strong magnetic field has been demonstrated (Sperber and Dransfeld, Naturwissenschaften V. 68; pp. 40-41, 1981).

Adey (Physiological Review (1981) V. 61, pp. 435-514) has presented a general review of tissue interactions with nonionizing electromagnetic fields. In this review Adey (ibid, p. 463) cites evidence that agarose, a bacterial polysaccharide, is affected in orientation by magnetic fields during an agarose gelation process. Agarose gelled in a 1.0 T magnetic field (apparently about 16,667 gauss) was about 7% more permeable to electrophoretically migrating bacterial DNA than was agarose gel formed at about 0.5 gauss.

Several polymers have been shown to adopt a particular orientation with respect to externally applied magnetic fields. Precipitation of collagen in a field of approximately 20 kilogauss resulted in highly ordered arrays of fibrils with their axes at right angles to the field (Murthy, Biopolymers V. 23; pp. 1261-1267, 1984). Increasing the field beyond 20 kilogauss increased the order of the fibrils. Skeletal muscle actin has also been shown to adopt a preferred orientation in strong magnetic fields (Torbet and Dickens, FEBS Letts V. 173 p. 403, 1984).

In U.S. Pat. No. 4,020,590, Davis describes an apparatus and method for exposing seeds to a magnetic field and thereby altering seed germination and plant growth therefrom. In U.S. Pat. No. 4,065,386 Rigby describes a method of algae growth control wherein water is passed through a magnetic field. Amburn in U.S. Pat. Nos. 3,910,233 and 3,991,714 describes methods and an apparatus for magnetically increasing the incidence of fertilization by fowl sperm and magnetically inducing greater hatching rates of fertilized eggs.

SUMMARY OF THE INVENTION

The present invention comprises a method of producing cellulose altered during its biosynthesis. Both eucaryotic and procaryotic cellulose-producing organisms, when subjected to a magnetic field substantially greater than 0.5 gauss, produce altered cellulose. The altered cellulose produced by procaryotic cells is amorphous, has an increased absorptivity for water and greater chemical reactivity. The procaryotic cells are preferably in a liquid medium comprising bacterial nutrients when subjected to the magnetic field. On the other hand, plant tissue, (eucaryotic cells), when exposed to a magnetic field, generates altered cellulose microfibril patterns. The disordered arrangement of cellulose microfibrils affects the mechanical strength and other physical characteristics of the cell wall.

DESCRIPTION OF PREFERRED EMBODIMENTS

Cellulose-producing microorganisms useful in the present invention include members of the Acetobacter, Rhizobium, Agrobacterium, Pseudomonas and Alcaligenes genera (Brown et al. J. Applied Polymer Science Appl. Polymer Symp. (1983) V. 37 pp. 33-78). The growth of such cellulose-producing microorganisms and the synthesis of cellulose occur generally in a suitable nutrient medium having a pH between about 3.5 and about 7.0 when incubated under aerobic conditions and at temperatures between about 20° C. and about 35° C. A use of *Acetobacter xylinum* to coat synthetic fibers with microbial cellulose is disclosed in U.S. Pat. No. 4,378,431, issued to Brown, which is incorporated by reference herein. Many varieties of cellulose-producing microorganisms, particularly *Acetobacter xylinum*, exist and are virtually ubiquitous in natural surroundings such as damp forests, for example.

According to Bergey's Manual of Systematic Bacteriology Vol. 1, (ed. N. R. Krieg pp. 268-274, Williams and Wilkins, Baltimore, Md. 1984) cellulose synthesizing Acetobacter strains which were formerly classified as *Acetobacter aceti*, subspecies xylinum are now classified as subspecies of *Acetobacter pasteurianus* and *Acetobacter hansenii*. The strain of *Acetobacter xylinum* utilized herein is synonymous with *Acetobacter aceti*, subspecies xylinum. The Bergey reference cited above also refers to studies indicating that static culture favors cellulose synthesizing cells while shake cultures favor cellulose-free mutant cells.

The plant tissue considered here includes specifically the grass, Avena. Avena is a typical vascular plant, and as such, has the capacity to synthesize cell walls of cellulose (Raven, Evert, and Curtis, "Biology of Plants", Worth Publishers, New York, 1976), hereafter referred to as "plant" cellulose.

The present invention comprises a process for altering microbial and plant cellulose during the production thereof by organisms. When cellulose-producing organisms are subjected to a magnetic field greater than that of the earth's magnetic field (i.e. about 0.5 gauss) during a period of cellulose production, the nature of their cellulose product is markedly altered. When such cellulose-producing microorganisms are removed from the magnetic field, their cellulose then produced is of a normal configuration and a return to the magnetic field results in a resumption of altered cellulose production.

Microbial cellulose produced under the influence of a magnetic field has an apparent crystallinity less than that normally found with microbial cellulose. The individual glucan chains interassociate with less force and order when formed in the presence of an effective magnetic field as judged by the ease of physically disrupting the resultant microfibril coalescence and the apparent decreased density and lack of microfibril bundle formation. The magnetically affected cellulose assumes a relatively amorphous configuration as compared to the normal and more orderly bundle or ribbon of microfibrils.

The magnetically altered form of microbial cellulose, having a much greater surface to volume ratio than that non-magnetically produced, has certain properties desirable for particular uses. For example, magnetically altered microbial cellulose has properties such as: (A) a greater capacity for water absorption; (B) greater chemical reactivity; (C) lower density; (D) lower tensile strength; (E) greater surface area; (F) and greater potential for graft copolymerization. Since the altered or amorphous cellulose glucan chains are less completely interassociated, the carbohydrate constituents thereof exhibit greater chemical reactivity in general. Such properties are of particular use in the development of effective absorbents and textile products having a variety of textures.

Plants exposed to magnetic fields significantly higher than 0.5 gauss do not exhibit normal cellulose microfibril deposition. Cellulose microfibrils in magnetic field treated tissue are deposited in considerable disarray. The highly ordered nature of deposition of plant cellulose is one of the major characteristics that determine the physical properties of cellulosic plant products (Preston, "The Physical Biology of Plant Cell Walls", Chapman & Hall, 1974). Magnetic field induced disruption of ordered deposition in plants provides a method for development of wood and textile products with different properties such as: materials with lower density, lower tensile strength, greater elasticity, or greater accessibility to chemical treatment or modifications. Random and disarrayed microfibrill or patterns result in the organism's cell walls having a lowered density and tensile strength.

The magnetically induced disarray of microfibrillar patterns will have further benefits as yet incompletely defined. One example of these further benefits is the production of houseplants whose normal patterns of growth and conformation have been modified by exposure to a magnetic field of at least 500 gauss. These plants of altered conformation will at least be of decorative use and interest to those studying magnetic influence on plant growth patterns.

The culture of cellulose-producing organisms in liquid nutrient medium and in a magnetic field substantially greater than 0.5 gauss may be performed to produce harvestable amounts of amorphous microbial cellulose. Said cellulose may be collected as a pellicle formed on a culture surface or by other means known by those skilled in the art. The particular amorphous structure of the cellulose produced, although microscopically apparent, is as yet incompletely defined.

The following specific examples are presented to more fully describe the present invention and are not meant to be limiting unless otherwise specifically designated in the accompanying claims.

EXAMPLE 1

*Acetobacter xylinum* Cellulose Production Under an Intense Magnetic Field

Bacterial cells of the species *Acetobacter xylinum*, American Type Culture Collection (ATCC) No. 23769 were taken from a single colony and inoculated in 5 ml of Schramm & Hestrin culture medium (J. General Biology V. 11, pp. 1233–129, 1954) containing: glucose, 10 g/l; peptone, 5 g/l; yeast extract, 5 g/l; anhydrous dibasic sodium phosphate, 2.7 g/l; and citric acid monohydrate, 1.15 g/l. The pH of the culture medium was adjusted to pH 6.0 and may be adjusted to between pH 3.5 and about pH 7.0 by addition of hydrochloric acid. The inoculated culture medium was aerobically incubated in an Erlenmeyer flask under static conditions for a period of five days. A pellicle comprising microbial cellulose was formed near the surface of the culture medium. The cellulosic pellicle was removed from the flask and washed with 50 mM pH 7.0 phosphate buffer containing 1 M glucose. *Acetobacter xylinum* cells were removed from the washed pellicle by physical disruption of the pellicle in pH 7.0 phosphate buffer containing 1 M glucose. The cells thus removed were placed in 10 mm thin walled sample tubes used for nuclear magnetic resonance studies. One tube of cells was inoculated at 31° C. as a control, and another tube of cells was placed in the 1.8 tesla ($1.8 \times 10^4$ gauss) magnetic field of a Varian FT80A nuclear magnetic spectrometer (Varian Inc.) The cells were incubated in the magnetic field at 31° C. for a total period of 30 minutes.

Samples were withdrawn after magnetic and control incubation periods of 12 minutes and 30 minutes. The 30 minute magnetically-incubated cells were removed from the magnetic field, incubated for a 10 minute period at about 31° C. in the absence of an artificial magnetic field, and then reintroduced into the magnetic field for a final 10 minute incubation, again at about 31° C. Cell samples were withdrawn after each of these 10 minute incubations.

*Acetobacter xylinum* cells and accompanying attached microbial cellulose in the withdrawn samples were subjected to negative staining with uranyl acetate and examined by electron microscopy. The results found with cells obtained after a 12 minute or 30 minute control incubation or magnetic incubation are summarized in Table 1.

With the control an electron micrograph showed uranyl acetate-stained *Acetobacter xylinum* producing a cellulose ribbon with normal, orderly fasciation of microfibrils in the absence of artificial magnetic fields. An electron micrograph showed uranyl acetate-stained *Acetobacter xylinum* producing, under the influence of a magnetic field (18,000 gauss for 30 minutes at 31° C.), cellulose as an amorphous mass. The amorphous cellulose mass is secreted from the cells as a web or blanket formation, rather than the normal orderly ribbon shown with the control.

TABLE 1

|  | Control | | Magnetically incubated | |
| --- | --- | --- | --- | --- |
|  | 12 min | 30 min | 12 min | 30 min |
| Percent cells without visible cellulose product | 45 | 71 | 69 | 74 |
| Percent cells with normal cellulose ribbon attached | 54 | 28 | 1 | 1 |
| Percent cells with amorphous cellulose attached | 1 | 1 | 30 | 25 |

A normal cellulose ribbon is produced by an orderly fasciation of cellulose microfibrils biosynthesized and secreted by Acetobacter cells. When cellulose biosynthesis and secretion occurred in the magnetic field, the microfibrils were not subject to orderly fasciation and formed an amorphous mass with little in the way of crystalline structure.

It was further determined that orderly fasciation resumed when the Acetobacter cells were removed from the magnetic field, the amorphous cellulose mass now becoming attached to the cells by a normal cellulose ribbon. Upon reintroduction into the magnetic field, amorphous cellulose production resumed resulting in cells with a chain of cellulose attachments, i.e., amorphous mass; cellulose ribbon; amorphous mass.

The amorphous nature of the magnetically induced cellulose product was found with Acetobacter cultures between about pH 4.8 and pH 7.0. It was also found that intermittent subjection of the cellulose-producing organisms to the magnetic field resulted in an increase in the incidence of cellulose microfibrillar disorder or amorphousness resulting from the magnetic field.

EXAMPLE 2

Structure of Amorphous Acetobacter Cellulose

The procedures and components described in Example 1 were utilized, but with the following modification. The *Acetobacter xylinum* cells were isolated in 50 mM, pH 7.0 phosphate buffer from the cellulosic pellicle and all incubations were at 32° C. The magnetic field was that of a Varian E-9 EPR Spectrometer, with a constant flux density of 6,000 gauss. Cells were incubated in succession for ten minutes in the magnetic field, ten minutes in the absence of the magnetic field, ten more minutes in the field, and finally ten minutes without the field. Samples of the cells were then subjected to treatment with colloidal gold particles or with the enzyme, cellobiohydrolase with adherent colloidal gold particles according to the method of Chanzy, et al. (1984, FEBS Letts, V. 172, pp. 193-197). An electron micrograph demonstrated the adherence of the gold-cellobiohydrolase to the amorphous cellulose. This adherence indicates the integrity of beta 1,4-linked glucan bonds in the amorphous cellulose. An electron micrograph demonstrated that colloidal gold particles alone have no specific adherence for the amorphous cellulose.

EXAMPLE 3

Amorphous Cellulose Production at 500 gauss and 6,000 gauss

Utilizing the instrumentation and procedures generally described in Example 2, *Acetobacter xylinum* cells were subjected to magnetic fields with the following modification. In one case, cells were subjected to a 500 gauss field for twenty minutes, followed by a ten minute 'rest' period without any artificial magnetism. Control cells were incubated for forty minutes in the absence of an artificial magnetic field. Electron micrographs of the various cells were obtained and examined. The data resulting from this examination are shown in Table 2.

TABLE 2

| | Effects of a 500 G magnectic field and intermittent exposure to 6000 G field in *Acetobacter xylinum* cellulose production. | | |
| --- | --- | --- | --- |
| Conditions of Treatment | 500 G field 20 minutes | 6000 G field for 10 minutes (2 exposures) with a 10 minute "recovery period" between exposures | 40 minutes |
| Percent of total cells exhibition no cellulose production | 41 | 63 | 89 |
| Percent of total cells producing a normal cellulose ribbon | 13 | 6 | 9 |
| Percent of total cells producing atypical/ amorphous cellulose | 46 | 31 | 3 |

*All cells were isolated 50 mM phosphate buffer, pH 7.0, and incubated in this buffer at 32 C during all treatments. Magnetic field treatments were followed by a 10 minute "recovery period" during which no field was applied.

As shown in Table 2, the extent of amorphous cellulose production is enhanced by both the 500 gauss magnetic field and the 6,000 gauss magnetic field. In addition, there is an overall stimulatory effect of magnetic fields on cellulose production, as yet incompletely understood.

EXAMPLE 4

Three day old seedlings of Avena sativa CV Garry, (Agway, Syracuse, N.Y.) were grown in the dark at 25° C. and were transferred to 10 mm thin-walled glass NMR tubes with a small amount of growth medium. Coleoptiles were oriented perpendicular to the field lines in a Varian FT80 spectrometer magnet (18,000 gauss) and exposed to the field for 30 minutes. Control plants were incubated at 31° C. for 30 minutes outside of the applied magnetic field. Coleoptiles were sliced into small segments directly after 30 minutes, immediately mounted on gold holders and frozen in freon cooled with liquid nitrogen. Specimens were fractured in a Balzers BA360 Freeze Fracture instrument (Balzers, Lichtenstein) and replicas were examined in a Philips 420 transmission electron microscope (Eindoven, Netherlands).

Cellulose microfibrils of Avena synthesized in the magnetic field were randomly organized and loosely associated with one another. This disarray was accompanied by extensive disruption of intramembranous particle distributions in the plasma membrane. Inner wall layers of control plants showed highly ordered, closely associated arrays of microfibrils that exhibited wall patterns typically found in Avena coleoptiles. Disruption in patterns of microfibril deposition in Avena was found to occur in magnetic fields with a field strength as low as 5,000 gauss.

An electron micrograph of freeze-fractured control Avena coleoptile plasma membrane outer leaflet indicated ordered and uniform cellulose microfibril impressions. The cellulose microfibril impressions from magnetically treated cells reflected that cellulose microfibrils demonstrate a random and disarrayed pattern which may lead to a lowered density of the material tensile strength and resulting from the applications of the artificial magnetic field.

Upon examination of the presently disclosed invention, it will be apparent to those skilled in the art that changes in the order of procedural steps and particular composition elements may be made without departing from the spirit and scope of the invention as described in the following claims.

What is claimed is:

1. A method of producing amorphous or disordered cellulose comprising:
    incubating a microorganism actively producing cellulose in the presence of a magnetic field greater than about 500 gauss; and
    collecting cellulose therefrom.

2. The method of claim 1 wherein the cellulose producing microorganism is defined further as being a procaryotic microorganism.

3. The method of claim 2 wherein the procaryotic microorganism is in a liquid culture medium having a pH between about pH 3.5 and about pH 7.0.

4. The method of claim 2 wherein the liquid culture medium is defined further as comprising bacterial nutrients.

5. The method of claim 2 wherein the procaryotic microorganism is of the genus Acetobacter, Rhizobium, Agrobacterium, Pseudomonas or Alcaligenes.

6. The method of claim 2 wherein the cellulose-producing microorganism is defined further as being *Acetobacter xylinum*, ATCC number 23769.

7. The method of claim 1 wherein the amorphous or disordered cellulose produced in the magnetic field is defined further as being microbial cellulose.

8. The method of claim 1 wherein the amorphous or disordered cellulose is defined further as having a water-absorptive capacity greater than cellulose produced in the absence of an artificial magnetic field.

9. The method of claim 1 wherein the amorphous or disordered cellulose is defined further as comprising incompletely interassociated glucose chains and being more susceptible to chemical reactants than cellulose produced in the absence of an artificial magnetic field.

10. The method of claim 1 wherein the magnetic field is defined further as being about 500 gauss.

11. The method of claim 1 wherein the magnetic field is defined further as being about 6,000 gauss.

12. The method of claim 1 wherein the magnetic field is defined further as being about 18,000 gauss.

13. The method of claim 1 wherein the incubating step is conducted in an intermittent magnetic field.

* * * * *